(12) United States Patent
Jin et al.

(10) Patent No.: US 10,166,099 B2
(45) Date of Patent: Jan. 1, 2019

(54) ARTIFICIAL HEART VALVE ANNULOPLASTY RING

(71) Applicant: KINGSTRONBIO (CHANGSHU) CO., LTD., Changshum, Jiangsu (CN)

(72) Inventors: Chang Jin, Jiangsu (CN); Shengping Sam Zhong, Jiangsu (CN)

(73) Assignee: KINGSTRONBIO (CHANGSHU) CO., LTD., Jiangsu (CN)

( * ) Notice: Subject to any disclaimer, the term of this patent is extended or adjusted under 35 U.S.C. 154(b) by 106 days.

(21) Appl. No.: 15/225,577

(22) Filed: Aug. 1, 2016

(65) Prior Publication Data

US 2016/0338830 A1 Nov. 24, 2016

Related U.S. Application Data

(63) Continuation of application No. PCT/CN2013/080328, filed on Jul. 29, 2013.

(51) Int. Cl.
*A61F 2/24* (2006.01)

(52) U.S. Cl.
CPC .......... *A61F 2/2445* (2013.01); *A61F 2/2448* (2013.01); *A61F 2220/0058* (2013.01); *A61F 2230/0091* (2013.01); *A61F 2250/0012* (2013.01); *A61F 2250/0018* (2013.01); *A61F 2310/00017* (2013.01); *A61F 2310/00023* (2013.01); *A61F 2310/00029* (2013.01)

(58) Field of Classification Search
CPC ..... A61F 2/2442; A61F 2/2445; A61F 2/2448
See application file for complete search history.

(56) References Cited

U.S. PATENT DOCUMENTS

| | | | | |
|---|---|---|---|---|
| 4,602,911 A * | 7/1986 | Ahmadi | ................ | A61F 2/2445 623/2.37 |
| 2003/0220686 A1* | 11/2003 | Arru | ..................... | A61F 2/2448 623/2.36 |
| 2007/0162112 A1* | 7/2007 | Burriesci | .............. | A61F 2/2448 623/2.36 |
| 2010/0152844 A1* | 6/2010 | Couetil | ................. | A61F 2/2448 623/2.36 |
| 2012/0136436 A1* | 5/2012 | Cabiri | ............... | A61B 17/0401 623/2.37 |
| 2013/0204361 A1* | 8/2013 | Adams | .................. | A61F 2/2445 623/2.37 |
| 2013/0226289 A1* | 8/2013 | Shaolian | ............... | A61F 2/2466 623/2.11 |

* cited by examiner

*Primary Examiner* — Thomas J Sweet
*Assistant Examiner* — Megan Wolf
(74) *Attorney, Agent, or Firm* — J.C. Patents

(57) ABSTRACT

The present invention provides an artificial heart valve annuloplasty ring, including an outer layer (6) and an annular main body (8) integrally formed from multiple ring sections, the outer layer (6) is a fiber fabric layer covered on the outside of the annular main body (8), the annular main body (8) includes a tube with a tube wall that has a slotted structure capable of adjusting the rigidity of the annuloplasty ring. The artificial heart valve annuloplasty ring provided in the present invention has a simple structure, easy-to-adjust rigidity, and does not need to separately design and manufacture a mold for the main body of the annuloplasty ring during manufacturing.

19 Claims, 8 Drawing Sheets

ARTIFICIAL HEART VALVE ANNULOPLASTY RING

CROSS-REFERENCE TO RELATED APPLICATIONS

This application is a continuation of International Application No. PCT/CN2013/080328 filed on Jul. 29, 2013. The contents of the above identified application are incorporated herein by reference in its entirety.

TECHNICAL FIELD

The present invention relates to an artificial heart valve annuloplasty ring, belonging to the technical field of medical device.

BACKGROUND

During heart systole, its mitral valve and tricuspid valve close up, forcing intraventricular blood to flow into arteries, and meanwhile preventing intraventricular blood from reversely flow into atriums. However, backflow of blood into the atriums occurs when contraction of ventricles fails to trigger full closure of the valve cusps due to diseases such as valve sinus dilation, rapture of mitral chordae tendinae, perforation of valve cusp or prolapse of valve cusp. Annuloplasty ring implantation, as an important clinical means to reshape diseased mitral valve and tricuspid valve to maintain their normal shape and contour, can be employed to repair ventricular regurgitation and the like due to disease-induced incomplete closure of the mitral valve and tricuspid valve cusps.

Currently, the annuloplasty ring already used for clinical purposes is mainly divided into three types: soft ring, rigid ring and semi-rigid ring. The soft ring is mainly of a two-dimensional structure and a main structure thereof is mainly made of a polymer material, so that soft ring can fit well with an annulus of a valve, but the material of the soft ring is excessively soft, which is not favorable for effective closure of the valve cusps and effective plastic of the ring. And the rigid ring and the semi-rigid ring are of a two-dimensional planar structure, or a three-dimensional saddle structure designed according to the anulus of the valve, in which the latter structure is advantageous in reducing stress imposed on the valve cusps and enhancing the durability. The rigid ring usually adopts a metal material and has good support strength, but such rigid ring is not easy to bend, therefore it is unable to achieve a coordination movement with the cardiac cycle. The semi-rigid ring combines the advantages of both the soft ring and the rigid ring, and can offer good support strength through adjusting rigidity of main body of the annuloplasty ring, and meanwhile effectively adapt to variation in the ring plane of the valve caused by cardiac systole and diastole. Therefore, the semi-rigid ring is brought into limelight.

Currently, regarding the semi-rigid ring, its annular main body mainly adopts a wire with a variable diameter, in order to adjust the rigidity, and the rigidities of ring sections are controlled through adjusting the diameter of the wire, but the process to design and manufacture a mold for manufacturing such a semi-rigid ring is tedious, resulting in a complicated manufacturing process and stringent technical requirements; sometimes, its annular main body adopts a combination of metal and polymer to adjust the rigidity of the entire annuloplasty ring, where a metallic ring section and a polymeric ring section need to be matched according to rigidity requirement before being connected, and it needs to strictly control processing and connecting procedure of the metallic ring section and the polymeric ring section due to requirements for special application environment, which leads to a complex process and an increased risk of failure; and furthermore, for some of such structure designs, wear and tear often occur at the connection of the metallic and the polymeric ring sections during application, affecting the long-term use effect.

SUMMARY

The present invention provides an artificial heart valve annuloplasty ring, which can meet requirements for application, has easy-to-adjust rigidity and simple structure, is easy to manufacture, and is able to maintain a long-term stable plastic effect.

The present invention provides an artificial heart valve annuloplasty ring including an outer layer and an annular main body that is integrally formed from multiple ring sections, wherein the outer layer is a fiber fabric layer covered on the outside of the annular main body, and the annular main body includes a tube with a tube wall that is provided with a slotted structure capable of adjusting rigidity of the annuloplasty ring.

The main body of the annuloplasty ring may have the same shape as in the prior art, namely, it may be integrally formed from multiple ring sections. For instance, it may include an anterior ring section, a posterior ring section, a left ring section, a right ring section and connection sections arranged therebetween, where the ring sections are an integrated structure, forming a closed or open annular main body together. The annular main body is externally covered with a biocompatible fiber fabric layer, which may be a polymer material meeting medical standards, for instance, a medical polyester fabric.

In accordance with the artificial heart valve annuloplasty ring provided in the present invention, the slotted structure is a helical slot formed along the circumference of the tube.

In accordance with the artificial heart valve annuloplasty ring provided in the present invention, the slotted structure is a combination of a helical slot formed along the circumference of the tube and holes distributed on the tube wall.

In the present invention, the purpose of changing and adjusting the rigidity of the annular main body is fulfilled through providing the tube wall of the ring body tube with the slotted structure. There is no special demands for concrete arrangement form of the slotted structure, for instance, the slotted structure may be holes distributed on the tube wall, helical slots formed along the circumference of the tube or the combination of them. The holes distributed on the tube wall may be through holes with different shapes, for instance, circular through holes, elliptical through holes, or polygonal through holes such as, triangular or square through holes, or combination thereof. Of course, taking processing convenience and guaranteeing characteristics of the tube into consideration, holes with a definite shape or varied little in shape may be chosen. In the present invention, the slotted structure may be one of the helical slots, the holes and other structures, or may be a combination thereof, so as to satisfy the rigidity requirement. In one particular embodiment of the present invention, the slotted structure may be a combination of the helical slots formed along the circumference of the tube and quadrilateral holes distributed on the tube wall. In accordance with the artificial heart valve annuloplasty ring provided in the present invention, the helical slots may have a single-helical, a double-helical or a multi-helical structure. The double-helical and the multi-helical structure may be composed of multiple single-helical structures with the same or different helical directions.

In accordance with the artificial heart valve annuloplasty ring provided in the present invention, the tube may be a single-layer tube, a double-layer tube or a multi-layer tube. In the present invention, the main body of the annuloplasty ring may be single-layer tube, or a double-layer or a multi-layer tube formed by inserting a tube with a smaller outer diameter into a tube with a larger inner diameter. Regarding an annuloplasty ring with a double-layer or a multi-layer tube, the same portion of each layer may adopt the same or different patterns; regarding an annuloplasty ring with a single-layer tube, holes and helical slots may be distributed on different ring sections of the tube, so as to realize different demands for rigidity of different ring sections, enabling the entire annuloplasty ring to match perfectly with the cardiac cycle.

In accordance with the artificial heart valve annuloplasty ring provided in the present invention, slotted rates of ring sections of the annular main body, the number of the layer of the tube, thickness of the tube wall and outer diameter of the tube may be adjusted individually or in combination, so as to obtain the annuloplasty ring with different rigidities. For instance, it can select and determine a tube with proper number of the layer, wall thickness and diameter to determine rigidity of the annuloplasty ring as a whole, and then the tube may be slotted wholly or partially so as to further adjust the rigidity of the annular main body through adjusting the slotted rate (i.e. adjusting pattern, position and/or density of the slotted structure). The slotted structure may be arranged on each of the ring sections, or selectively arranged on a certain ring section or certain ring sections, and the slotted rate of the slotted structure on different ring sections may be the same or different. It could be understood that, rigidities of the ring sections of the annuloplasty ring are different or not all the same, which is more conducive to clinical application. The slotted rate and slotted pattern of the entire tube and/or each ring section may be adjusted to adjust and meet different rigidity requirements of the ring sections of the annuloplasty ring. For instance, a ring section requiring high rigidity may adopt a low slotted rate, or even not be slotted, and a ring section requiring a low rigidity may adopt a high slotted rate.

The "slotted rate" used in the present invention refers to percentage of an area of the side wall that is slotted accounting for the entire side wall of a corresponding ring section of a tube. The slotted rate may be achieved through designing the shape, size and distribution of the holes, or density and slot width of the helical slots.

In accordance with the artificial heart valve annuloplasty ring provided in the present invention, generally, the tube may have an outer diameter of 0.6-3 mm, and a wall thickness of 0.1-1 mm. With respect to an annuloplasty ring with a double-layer or a multi-layer tube, the outer diameter may be interpreted as the outer diameter of the outmost tube, and the wall thickness may be interpreted as the sum of wall thicknesses, i.e., overall wall thickness, of tubes of a double-layer or a multi-layer tube.

In accordance with the artificial heart valve annuloplasty ring provided in the present invention, the tube may be all kinds of medical alloy tubes or polymer tubes, including a medical nickel titanium alloy tube, a cobalt chromium alloy tube, a titanium alloy tube, a stainless steel tube or a polymer tube. For instance, the alloy tube may be made of stainless steel No. 316L, cobalt chromium alloy No. MP35, L605, Elgiloyor Phynox, titanium alloy Ti6Al4V, or nickel titanium alloy Ni—Ti; and the polymer tube, for instance, may be made of polyethylene, polytetrafluoroethylene, polyformaldehyde resin or polyethylene terephthalate and the like.

In accordance with the artificial heart valve annuloplasty ring provided in the present invention, the slotted structure on the tube may be formed by any suitable method, where a laser cutting method is preferred due to requiring no additional fixture and having high processing efficiency. When manufacturing the annuloplasty ring according to the present invention, firstly a tube with a desired length may be cut, and a pattern with a desired density and structure is formed on the tube through laser cutting or other methods, and then a final contour of the tube is obtained through a mold; or alternatively, after a final contour of the tube is obtained, a pattern with a desired density and structure is formed through three-dimensional flexible laser cutting or other methods. When the above processing method is used to adjust the rigidity of the annuloplasty ring, it does not need to redesign and manufacture a mold for the main body of the annuloplasty ring, and therefore is simple and convenient.

In accordance with the artificial heart valve annuloplasty ring provided in the present invention, the annuloplasty ring may be an open or closed mitral valve annuloplasty ring and has a two-dimensional or a three-dimensional structure, for instance, a structure with a C or D shaped projection on a plane.

In accordance with the artificial heart valve annuloplasty ring provided in the present invention, the three-dimensional structure may be a saddle structure, such structure better conforms to requirement of physiological structure of mitral valve, and is more conducive to fitting the annuloplasty ring with the mitral valve in the cardiac cycle.

In accordance with the artificial heart valve annuloplasty ring provided in the present invention, the annuloplasty ring is a tricuspid valve annuloplasty ring and has an open two-dimensional or three-dimensional structure.

The annuloplasty ring of the present invention may be not different in contour from that already used in clinical application or recorded, for instance, the annuloplasty ring disclosed in the Chinese patent No. CN101374478A entitled "annuloplasty ring for mitral valve prolapse".

In accordance with the artificial heart valve annuloplasty ring provided in the present invention, a middle layer may be further arranged between an outer layer and the annular main body of the annuloplasty ring. The middle layer is typically made of silicone, so as to facilitate suturing the annuloplasty ring to the heart, and meanwhile endowing the internal tube structure with better bending and rebounding performance, thereby fixing and effectively stabilizing the tube. The middle layer may adopt a circular tube, which is directly sleeved over the annular main body, or the middle layer is fixed to the outside of the annular main body in the form of a coating, a heat shrinkable pipe or a heat shrinkable film.

In accordance with the artificial heart valve annuloplasty ring provided in the present invention, the middle layer has a cuff where the annuloplasty ring is sewed to the heart (also referred to as "sewing cuff"), which is more favorable for suturing of the annuloplasty ring to a heart tissue during an implantation surgery. The sewing cuff may be integrally formed with the middle layer (via a mold). Additionally, the middle layer may be formed by using a soft tube with an inner diameter larger than the outer diameter of the tube, or a soft sheet with a size larger than the circumference of the tube (the size of the soft sheet is larger than what is required for completely covering the tube) to cover the outside of the tube, and the above sewing cuff margin is formed from an excess part of the middle layer, for instance, by folding and suturing.

In accordance with the artificial heart valve annuloplasty ring provided in the present invention, the middle layer and the outer layer are an integrated structure, and the outer layer is formed within the middle layer. The middle layer may be combined with the outer layer. For instance, an outer layer material (for instance, a polyester fiber material) with a wire or net single-layer or multi-layer structure is formed inside a middle layer material (for instance, silicone), and such a structure is favorable for enhancing the strength of the middle layer, as well as reducing the size of the annuloplasty ring. Furthermore, such a structure may merely serve as the middle layer, or may take the place of both the middle layer and the outer layer. In such structure, the sewing cuff may be formed by using the soft tube or soft sheet as the middle layer as described above, to cover the outside of the annular main body, or alternatively, by integration formation of the middle layer and outer layer.

In accordance with the artificial heart valve annuloplasty ring provided in the present invention, the annular main body is further internally provided with a wire capable of assisting in adjustment of the rigidity of the annuloplasty ring. Especially, the annular main body is internally provided with a wire when the annular main body has a high slotted rate, so as to maintain length and shape of the annular main body constant, and assist in adjusting the rigidity of the annuloplasty ring. The wire generally has a length not larger than that of the tube of the annular main body and thus may be arranged within the tube of the annular main body. The wire may be continuously or discontinuously arranged in the annular main body tube. Using the wire can effectively prevent change in structure of the annuloplasty ring during the course of three-dimensional setting and application after being cut, limit the extension and contraction lengths of the annuloplasty ring, and prevent the case where the valve cusps cannot be limited effectively after prolonged use. The material of the wire may be a medial metallic material or a medical polymer material, and the wire may be arranged in a conventional manner, without limitation in the present invention.

In accordance with the artificial heart valve annuloplasty ring provided in the present invention, the annular main body is a closed ring, the closure may be achieved by fixing, such as suturing, binding, welding or sleeving at a closing connection part of the annuloplasty ring. In a specific embodiment, the closing connection part of the tube is internally provided with a core, and closure of the annular main body may be achieved through such as interference fit, welding, suturing, binding or sleeving between the core and the tube. The core may be made of a medical metallic material or a medical polymer material, without restriction in the present invention. In another specific embodiment, closure of the annular main body is achieved by butt welding at the closing connection part of the tube.

The embodiments of the present invention at least have the following advantages:
1. The artificial heart valve annuloplasty ring of the present invention adopts a slotted tube as main body thereof, has simple structure and easy-to-adjust rigidity; and
2. According to the artificial heart valve annuloplasty ring of the present invention, which is used for repairing the artificial heart valve, when adjusting the rigidity of the annuloplasty ring, there is no need to redesign or manufacture a mold of the main body of the annuloplasty ring, leading to a simple and convenient processing method and a high productivity of qualified products.

Figure 1:
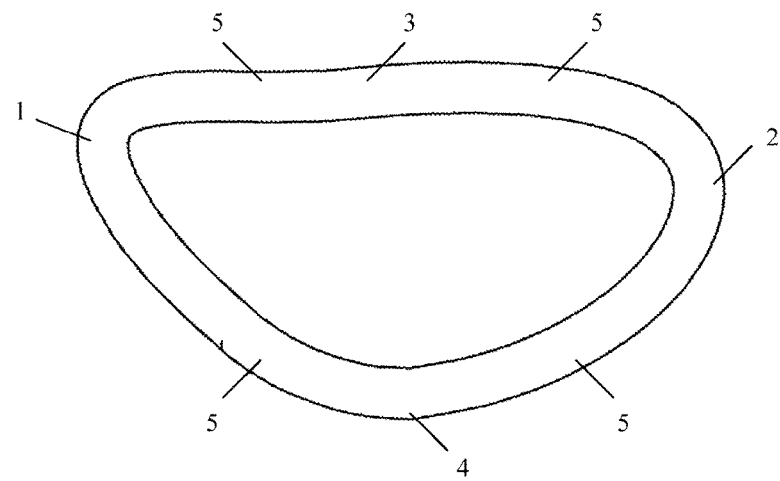
FIG. 1 is a diagram illustrating a mitral valve annuloplasty ring according to an embodiment of the present invention.

DESCRIPTION FOR REFERENCE SIGNS IN DRAWINGS 1 anterior ring section
2 posterior ring section
3 left ring section
4 right ring section
5 connection section 6 outer layer
7 middle layer
8 main body
9 wire
10 core
11 septal ring section
12 cuff

DETAILED DESCRIPTION

The present invention will be described in further detail in combination with specific embodiments and examples, the purpose is to help readers to better understand the substantive content of the present invention, and shall not be construed as restrictions to the scope of the present invention by any means.

Embodiment 1

This embodiment provides an artificial mitral valve annuloplasty ring. As shown in FIG. 1, the mitral valve annuloplasty ring has a closed three-dimensional saddle structure, and has an annular main body that is formed from an anterior ring section 1, a posterior ring section 2, a left ring section 3 and a right ring section 4. A high arched bulge of the annuloplasty ring is the anterior ring section 1, a low bulge is the posterior ring section 2, two concave sections are the left ring section 3 and the right ring section 4, respectively, a connection section 5 is respectively arranged between two adjacent ring sections among the anterior ring section 1, the left ring section 3, the posterior ring section 2 and the right ring section 4.

Figure 2:
FIG. 2 is an unfolded diagram illustrating a tube as a main body of a mitral valve annuloplasty ring according to an embodiment of the present invention.

As shown by FIG. 2, taking the midpoint of the posterior ring section 2 as a connection point, the annuloplasty ring is spread into a flat and straight tube along the circumference. The tube thereof is cut by laser to form a pattern in the form of helical slot, and the slotted rate of the ring sections (density of the helical slots) are adjusted so as to facilitate movement of the annuloplasty ring in coordination with the cardiac cycle when the heart contacts and expands. As shown in FIG. 2, the posterior ring section 2, the left ring section 3 and the right ring section 4 are soft ring sections with the highest slotted rate; the anterior ring section 1, relative to the posterior ring section 2, the left ring section 3 and the right ring section 4, is a rigid ring section with the lowest slotted rate; the connection section 5 has a slotted rate that is between the slotted rates of two ring sections connected by the connection section 5.

Figure 3:
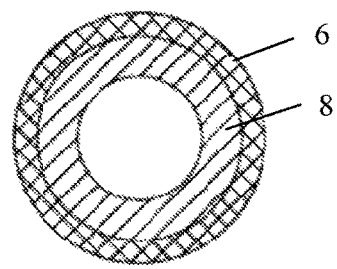
FIG. 3 is a diagram illustrating cross-section structure of a mitral valve annuloplasty ring according to an embodiment of the present invention.

FIG. 3 is a cross-section diagram of the annuloplasty ring, where the tube uses a medical nickel titanium alloy tube as its main body 8, an outer layer 6 is a medical polyester fiber fabric with excellent biocompatibility, and may connect with the heart through suturing in surgery.

Figure 4:
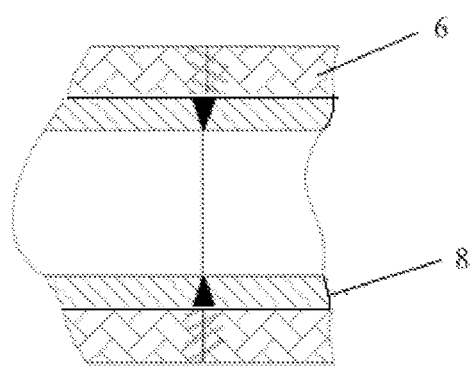
FIG. 4 is a longitudinal section diagram of a closing connection part of a mitral valve annuloplasty ring according to an embodiment of the present invention.

FIG. 4 is a longitudinal section diagram illustrating a closing connection part of the annuloplasty ring. A medical nickel titanium alloy tube as the main body 8 is closed through butt welding at the closing connection part thereof, thereby realizing closure of the annuloplasty ring; the medical polyester fiber fabric of the outer layer 6 directly covers the outside of the medical nickel titanium alloy tube 8 through suturing.

The artificial mitral valve annuloplasty ring provided in the embodiment is composed of multiple ring sections with different slotted rates along its circumference, and thereby forms four movement units in the anterior, posterior, left and right of the annuloplasty ring, respectively, due to different rigidities. The anterior ring section 1 with a low slotted rate (a large rigidity) is mainly used to maintain curvature of the saddle structure of a physiological mitral valve ring simulated by the artificial mitral valve annuloplasty ring, while the posterior ring section 2, the left ring section 3 and the right ring section 4 with a large slotted rate (a small rigidity) correspond to the anterior ring section 1 such that the movement pattern of the artificial mitral valve annuloplasty ring is consistent with that of the physiological mitral valve ring, so as to meet the requirement of the latter; and the connection section 5 functions as stress buffer among the above ring sections. Therefore, the artificial mitral valve annuloplasty ring of this embodiment can move in coordination with each cardiac cycle during heart pulsation.

Embodiment 2

This embodiment provides an artificial mitral valve annuloplasty ring, the shape of which is the same as that of the artificial mitral valve annuloplasty ring in Embodiment 1, as shown in FIG. 1.

Figure 5:
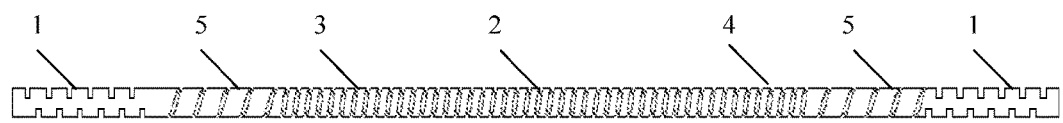
FIG. 5 is a diagram illustrating a tube as a main body of a mitral valve annuloplasty ring according to another embodiment of the present invention.

As shown in FIG. 5, taking the midpoint of the anterior ring section 1 as a connection point, the annuloplasty ring is spread into a flat and straight tube along its circumference. The tube thereof is cut by laser to form square and helical slotted patterns, where the ring sections have different slotted rates and patterns. As shown in FIG. 5, an anterior ring section 1 is rigid, and has a square-hole slotted structure and the lowest slotted rate; a left ring section 3 and a right ring section 4 have a rigidity smaller than that of the anterior ring section 1, i.e., the former two ring sections have a slotted rate lower than that of the anterior ring section 1, and the former two ring sections have a helical slotted structure; a posterior ring section 2 has a smaller rigidity than the anterior ring section 1, the left ring section 3 and the right ring section 4, and has a helical slotted structure and the highest slotted rate; as shown in FIG. 5, a connection section 5 has a slotted rate that is between the slotted rates of two ring sections connected by the connection section 5. The ring sections with different slotted rates cooperate with each other and thus provide a desired rigidity for the annuloplasty ring.

Figure 6:
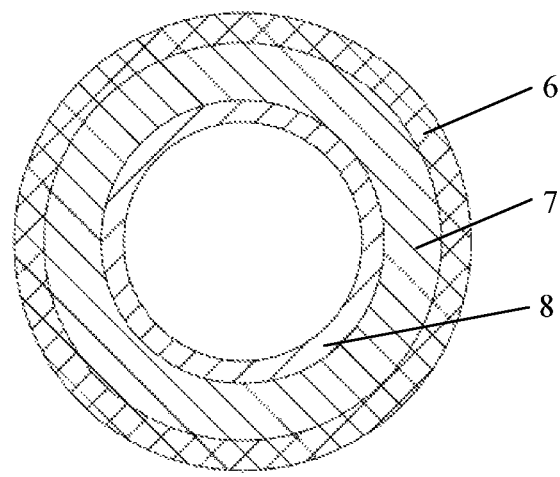
FIG. 6 is a diagram illustrating cross-section structure of a mitral valve annuloplasty ring according to another embodiment of the present invention.

As shown in FIG. 6, in the artificial mitral valve annuloplasty ring provided in this embodiment, a middle layer 7, which is a silicone tube, is arranged between an outer layer 6 (a polyester fiber fabric layer) and a main body 8, and the main body 8 is a medical nickel titanium alloy tube.

Figure 7:
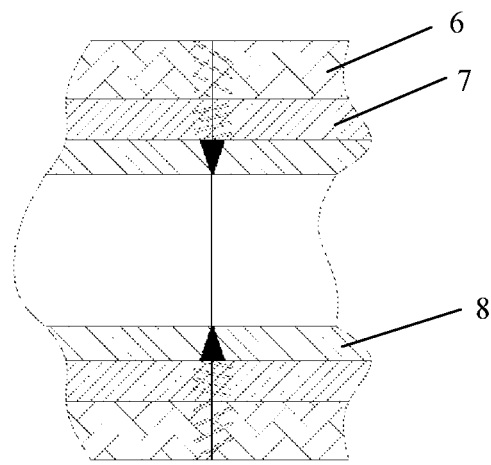
FIG. 7 is a longitudinal section diagram of a closing connection part of a mitral valve annuloplasty ring according to another embodiment of the present invention.

FIG. 7 is a longitudinal section diagram illustrating a closing connection part of the annuloplasty ring, where a medical nickel titanium alloy tube 8 as the innermost layer is closed via butt welding; the middle layer 7 is tightly sleeved on the outside of the medical nickel titanium alloy tube 8, and is closed by suturing at joint points thereof, the outer layer 6 is a medical polyester fiber fabric and is directly covered on the outside of the silicone tube as the middle layer 7 through suturing.

The artificial mitral valve annuloplasty ring provided in this embodiment is capable of moving in coordination with each cardiac cycle during heart pulsation and is provided with a middle layer so as to facilitate suturing of the annuloplasty ring to the heart in an implantation surgery.

Embodiment 3

This embodiment provides an artificial mitral valve annuloplasty ring, with the entire shape thereof and the structure of the annular main body being the same as in Embodiment 2.

Figure 8:
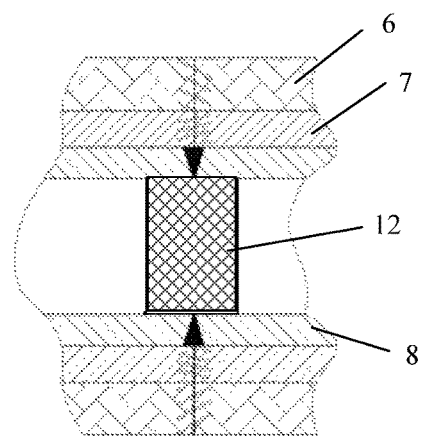
FIG. 8 is a longitudinal section diagram of a closing connection part of a mitral valve annuloplasty ring according to yet another embodiment of the present invention.

As shown in FIG. 8, in the artificial mitral valve annuloplasty ring provided in this embodiment, an outer layer 6 is a polyester fiber fabric, a middle layer 7 is a silicone tube, and both the outer layer 6 and the middle layer 7 are closed via suturing. A main body 8 is a medical linear polyformaldehyde resin tube (brand name: Delrin, produced by DuPont Chemical Group CO., Ltd. (Branch in China)), and a core 12 is provided at a closing connection part in the tube of the main body 8, and the core 12 is also made of a medical linear polyformaldehyde resin and is welded onto an inner wall of the tube of the main body 8 through ultrasonic welding, so as to guarantee closure of the tube of the main body 8.

Embodiment 4

This embodiment provides an artificial mitral valve annuloplasty ring, the shape of which is the same as that of the artificial mitral valve annuloplasty ring in Embodiment 1, as shown in FIG. 1.

Figure 9:
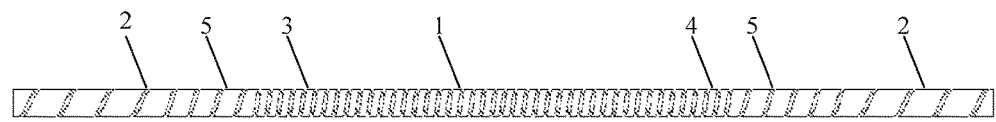
FIG. 9 is a diagram illustrating a tube as a main body of a mitral valve annuloplasty ring according to yet another embodiment of the present invention.

As shown in FIG. 9, taking the midpoint of a posterior ring section 2 as a closing connection point, the main body 8 of the annuloplasty ring is spread into a flat and straight tube along its circumference. The tube thereof is cut by laser to form helical slotted patterns, where the ring sections have different slotted rates. A anterior ring section 1, a left ring section 3 and a right ring section 4 are soft and have the highest slotted rate; the posterior ring section 4, relative to the anterior ring section 1, the left ring section 3 and the right ring section 4, is rigid and has the lowest slotted rate; a connection section 5 has a slotted rate that is between those of two ring sections connected by the connection section 5.

Figure 10:
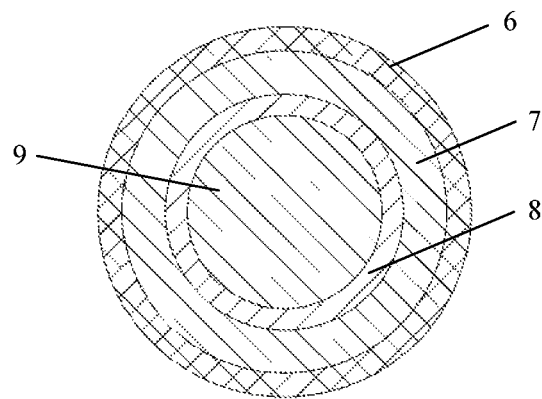
FIG. 10 is a diagram illustrating a cross-section structure of a mitral valve annuloplasty ring according to yet another embodiment of the present invention.

As shown in FIG. 10, an outermost layer 6 of the artificial mitral valve annuloplasty ring provided in this embodiment is a polyester fiber fabric, a middle layer 7 is a silicone tube, the main body 8 is a medical cobalt chromium alloy tube with a cobalt chromium alloy wire 9 arranged therein.

Figure 11:
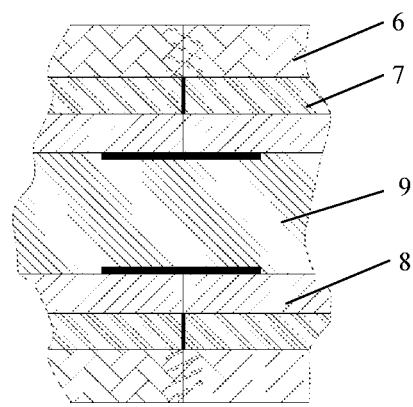
FIG. 11 is a longitudinal section diagram of a closing connection part of a mitral valve annuloplasty ring according to yet another embodiment of the present invention.

FIG. 11 is a longitudinal section diagram illustrating a closing connection part of the annuloplasty ring. The medical cobalt chromium alloy tube as the main body 8 is directly welded to the cobalt chromium alloy wire 9; the silicone tube as the middle layer 7 is tightly sleeved on the outside of the medical nickel titanium alloy tube 8, and is closed at joint points via butt binding using an adhesive with biocompatibility, the outer layer 6 is a medical polyester fiber fabric, and is directly covered on the outside of the silicone tube 7 through suturing.

The mitral valve annuloplasty ring provided in this embodiment is favorable for maintaining a physiological saddle shape which varies with the cardiac cycle, and ensuring butt-connection quality of the valve cusps, besides, use of the wire can effectively prevent change in structure of the annuloplasty ring during three-dimensional setting and application after being cut, and limit the maximum contraction and extension lengths of the annuloplasty ring, thereby preventing failure to effectively limit the valve cusps after long-term use.

Embodiment 5

Figure 12:
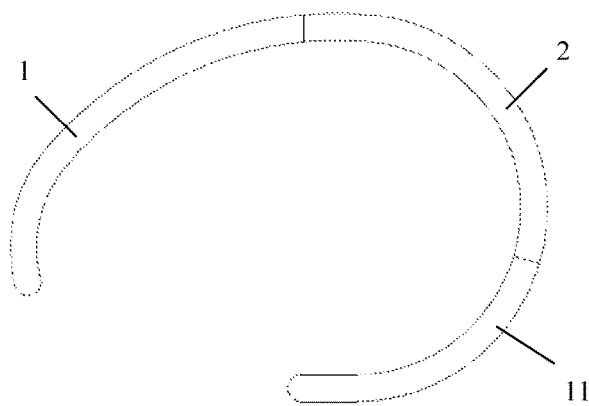
FIG. 12 is a diagram illustrating a tricuspid valve annuloplasty ring according to yet another embodiment of the present invention.

This embodiment provides an artificial tricuspid valve annuloplasty ring, which has a three-dimensional structure consistent with the physiological shape of a tricuspid valve, and the projection thereof on a plane is shown in FIG. 12. The annuloplasty ring is composed of an anterior ring section 1, a posterior ring section 2 and a septal ring section 11.

Figure 13:
FIG. 13 is an exploded diagram illustrating a tube as a main body of a tricuspid valve annuloplasty ring according to yet another embodiment of the present invention.

As shown in FIG. 13, the annuloplasty ring is spread into a flat and straight tube along its circumference, and the tube thereof is cut by laser to form a helical slotted pattern, where the ring sections have different slotted rates and patterns.

Figure 14:
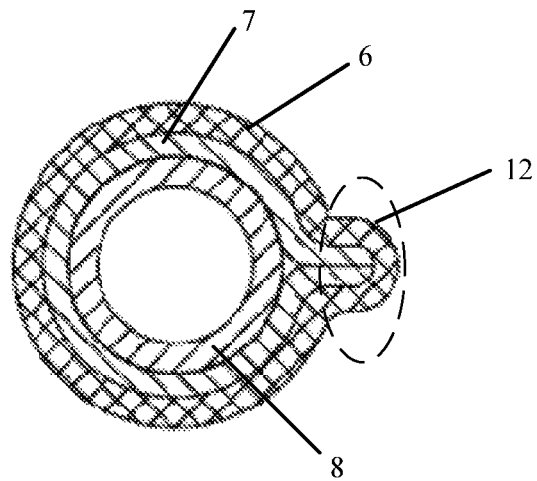
FIG. 14 and FIG. 15 are diagrams illustrating cross-section structure of a tricuspid valve annuloplasty ring with a sutural margin according to an embodiment of the present invention.
Figure 15:
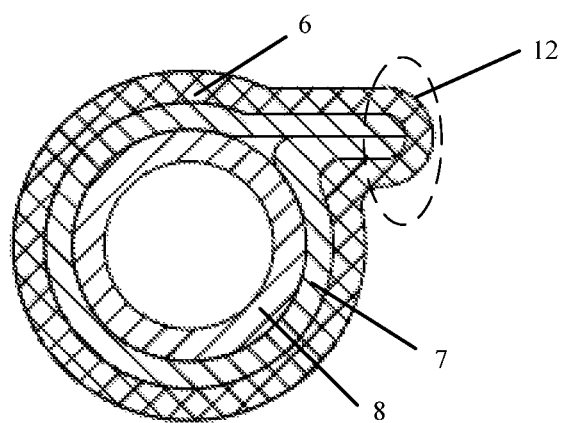

In the artificial tricuspid valve annuloplasty ring provided in this embodiment, an outer layer 6 is a polyester fiber fabric, a middle layer 7 is a silicone tube with an inner diameter larger than an outer diameter of the tube of a main body tube, and a main body 8 is a medical nickel titanium alloy tube. The excess parts of the middle layer 7 and the outer layer 6 may be sutured to form a cuff 12 to be sutured to the heart during implantation. The specific structure of the cross-section of the annuloplasty ring is shown in FIG. 14 or FIG. 15. Both ends of the middle layer 7 and the outer layer 6 are directly sutured to enclose the main body tube 8 therein.

The tricuspid valve annuloplasty ring provided in the embodiment is conducive to maintaining a physiological three-dimensional shape varying with the cardiac cycle, and guaranteeing coaptation quality of the valve cusps, and thus may be applied in clinical plastic repair surgery of tricuspid valve, and achieve a coordinated movement with the cardiac cycle.

Embodiment 6

This embodiment provides an artificial mitral valve annuloplasty ring, the shape of which is the same with that of the artificial mitral valve annuloplasty ring in Embodiment 1, as shown in FIG. 1. The annuloplasty ring has an anterior ring section 1, a posterior ring section 2, a left ring section 3, a right ring section 4 and connection sections 5, which have the same slotted rates as corresponding sections of the annuloplasty ring in Embodiment 1.

Figure 16:
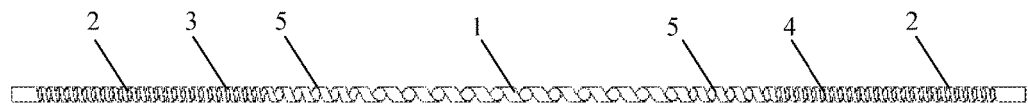
FIG. 16 is an unfolded diagram illustrating a tube as an inner-layer of a main body of a mitral valve annuloplasty according to yet another embodiment of the present invention.
Figure 17:
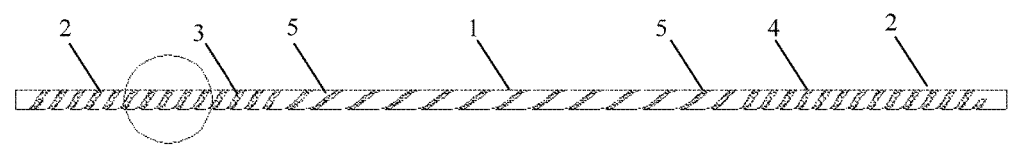
FIG. 17 is an exploded diagram illustrating a tube as an outer layer of a main body of a mitral valve annuloplasty ring according to yet another embodiment of the present invention.
Figure 18:
FIG. 18 is a partial enlargement diagram illustrating a double-helical structure formed by slotting on the tube as an outer layer shown in FIG. 17.

What differs from Embodiment 1 is that, the artificial mitral valve annuloplasty ring in this embodiment has an annular main body with a double-layer tube structure. As shown in FIG. 16, the inner layer tube has an outer diameter of 1.4 mm, and a left-handed helical structure slotted thereon; as shown in FIG. 17, the outer layer tube is a tube with an inner diameter of 1.4 mm to be matched with the inner layer tube, and has a right-handed double-helical structure slotted thereon. FIG. 18 is a local enlargement diagram of the double-helical structure shown in FIG. 17. After the above inner layer tube and the outer layer tube are cut to form desired patterns through laser, the inner layer that is a narrower tube is inserted into the outer layer that is a thicker tube, and then the two tubes integrally form the shape of the annular main body in Embodiment 1. Then, the inner layer tube is welded onto the core therein via the same manner as in Embodiment 3, and then the outer layer tube is subjected to butt welding via the same manner as in Embodiment 1, so as to form the desired closed ring structure.

The artificial mitral valve annuloplasty ring provided in this embodiment has an annular main body with a double-layer tube structure, and adopts double-layer opposite helixes, which is easier to adjust strength of the annuloplasty ring having a helical structure as well as enhancing durability of the annuloplasty ring.

Finally, it should be noted that the above embodiments are merely provided for describing rather than limiting the technical solutions of the present invention. It should be understood by persons skilled in the art that although the present invention has been described in detail with reference to the foregoing embodiments, modifications can be made to the technical solutions described in the foregoing embodiments, or equivalent replacements can be made to part or all technical features in the technical solutions; however, such modifications or replacements do not cause the essence of corresponding technical solutions to depart from the scope of the embodiments of the present invention.

What is claimed is:

1. An artificial heart valve annuloplasty ring, comprising an outer layer and an annular main body integrally formed from multiple ring sections, the outer layer being a fiber fabric layer covering the outside of the annular main body, wherein the annular main body comprises a tube with a solid tube wall that is provided with a slotted structure capable of adjusting rigidity of the annuloplasty ring, the slotted structure comprises helical slots formed along the circumference of the tube, and the helical slots have a double-helical or a multi-helical structure.

2. The artificial heart valve annuloplasty ring in accordance with claim 1, wherein, the slotted structure is a combination of the helical slots formed along the circumference of the tube and holes distributed on the tube wall.

3. The artificial heart valve annuloplasty ring in accordance with claim 2, wherein the slotted structure is a combination of the helical slots formed along the circumference of the tube and quadrilateral holes distributed on the tube wall.

4. The artificial heart valve annuloplasty ring in accordance with claim 1, wherein the tube is a single-layer tube, a double-layer tube or a multi-layer tube.

5. The artificial heart valve annuloplasty ring in accordance with claim 1, wherein slotted rates of the multiple ring sections of the annular main body, a number of layers of the tube, thickness of the tube wall and outer diameter of the tube are capable of being adjusted individually or in combination, so as to obtain the annuloplasty ring with different rigidities.

6. The artificial heart valve annuloplasty ring in accordance with claim 1, wherein the outer diameter of the tube is 0.6-3 mm, and the thickness of the tube wall is 0.1-1 mm.

7. The artificial heart valve annuloplasty ring in accordance with claim 1, wherein the tube is a medical nickel titanium alloy tube, a cobalt chromium alloy tube, a titanium alloy tube, a stainless steel tube or a polymer tube.

8. The artificial heart valve annuloplasty ring in accordance with claim 1, wherein the slotted structure is formed through laser cutting.

9. The artificial heart valve annuloplasty ring in accordance with claim 1, wherein the artificial heart valve annuloplasty ring is an open or closed mitral valve annuloplasty ring, and has a two-dimensional or a three-dimensional structure.

10. The artificial heart valve annuloplasty ring in accordance with claim 9, wherein the three-dimensional structure is a saddle structure.

11. The artificial heart valve annuloplasty ring in accordance with claim 1, wherein the artificial heart valve annuloplasty ring is a tricuspid valve annuloplasty ring, and has an open two-dimensional or three-dimensional structure.

12. The artificial heart valve annuloplasty ring in accordance with claim 1, wherein a middle layer is further arranged between the outer layer and the annular main body of the annuloplasty ring.

13. The artificial heart valve annuloplasty ring in accordance with claim 12, wherein the middle layer has a cuff for suturing the annuloplasty ring to the heart.

14. The artificial heart valve annuloplasty ring in accordance with claim 13, wherein the cuff is formed integrally with the middle layer.

15. The artificial heart valve annuloplasty ring in accordance with claim 13, wherein the middle layer is formed by using a soft tube with an inner diameter greater than the outer diameter of the tube or a soft sheet with a size larger than the circumference of the tube to cover the outside of the tube, and the cuff is formed from an excess part of the middle layer.

16. The artificial heart valve annuloplasty ring in accordance with claim 13, wherein the middle layer and the outer layer are an integrated structure, and the outer layer is formed outside the middle layer.

17. The artificial heart valve annuloplasty ring in accordance with claim 1, wherein the annular main body is further internally provided with a wire capable of assisting in adjustment of the rigidity of the annuloplasty ring.

18. The artificial heart valve annuloplasty ring in accordance with claim 1, wherein the annular main body is a closed ring, and a closing connection part of the tube is internally provided with a core, and closure of the annular main body is achieved through interference fit or welding between the core and the tube.

19. The artificial heart valve annuloplasty ring in accordance with claim 1, wherein the annular main body is a closed ring, and closure of the annular main body is achieved by butt welding at a closing connection part of the tube.

* * * * *